United States Patent [19]

Sozzi et al.

[11] 4,332,790

[45] Jun. 1, 1982

[54] MICROCAPSULE CONTAINING A MICROORGANISM AND A PROCESS FOR ITS PRODUCTION

[75] Inventors: Tomaso Sozzi, Lausanne; Alfred Schrenk, Orbe; Marcel Buhler, Tolochenaz, all of Switzerland

[73] Assignee: Societe d'Assistance Technique pour Produits Nestle S.A., Lausanne, Switzerland

[21] Appl. No.: 96,771

[22] Filed: Nov. 23, 1979

[30] Foreign Application Priority Data

Dec. 5, 1978 [CH] Switzerland ............. 12392/78

[51] Int. Cl.³ ............. A61K 39/02; A61K 9/50; A61K 9/42
[52] U.S. Cl. ............. 424/38; 424/92
[58] Field of Search ............. 424/38, 92, 93

[56] References Cited

U.S. PATENT DOCUMENTS

| | | | |
|---|---|---|---|
| 952,418 | 3/1910 | Collett et al. | 424/93 |
| 1,758,937 | 5/1930 | Earp-Thomas | 424/93 |
| 1,851,165 | 3/1932 | Farr | 424/93 |
| 1,929,085 | 10/1933 | Suehs | 424/93 |
| 2,369,218 | 2/1945 | Dick et al. | 424/38 |
| 2,875,130 | 2/1959 | Grass et al. | 424/38 |
| 3,072,528 | 1/1963 | Kludas et al. | 424/93 |
| 3,119,742 | 1/1964 | Heimlich | 424/38 |
| 3,265,629 | 8/1966 | Jensen | 424/38 |
| 3,369,969 | 2/1968 | Nouvel | 424/93 |
| 3,541,204 | 11/1970 | Sibbald et al. | 424/38 |
| 3,567,821 | 3/1971 | Nouvel | 424/93 |
| 3,726,805 | 4/1973 | Maekawa et al. | 424/38 |
| 3,804,776 | 4/1974 | Yazawa et al. | 424/38 |
| 3,823,228 | 7/1974 | Ferris et al. | 424/93 |
| 3,856,699 | 12/1974 | Miyano et al. | 424/38 |
| 3,957,974 | 5/1976 | Hata | 424/93 |
| 3,959,493 | 5/1976 | Baalsrud et al. | 424/38 |
| 3,960,757 | 1/1976 | Morishita et al. | 424/38 |
| 4,102,806 | 7/1978 | Kondo et al. | 424/93 |
| 4,132,753 | 1/1979 | Blichare et al. | 424/38 |
| 4,147,773 | 4/1979 | Ogasa | 424/93 |

FOREIGN PATENT DOCUMENTS

| | | |
|---|---|---|
| 2645444 | 4/1978 | Fed. Rep. of Germany . |
| 49-48731 | 12/1974 | Japan . |
| 53-32160 | 3/1978 | Japan . |
| 54-05092 | 1/1979 | Japan . |
| 54-35210 | 3/1979 | Japan . |
| 1271674 | 4/1972 | United Kingdom . |
| 598629 | 3/1978 | U.S.S.R. . |

OTHER PUBLICATIONS

Chem. Abstr. 90:166588f (1979) Miyairi, 89:135839p (1978) Ogasa, 89:58551j (1978) Mutai, 88:141708r (1978) Ogasa, 82:168858c (1975) Ikeda et al, 77:79557h (1972) Nisshin Flour.

Chem. Abstr., 91:62736g (1979) Seo et al, 90:12314b (1979) Kondo et al, 89:30765h (1978) Kondo et al, 89:12181k (1978) Theurer, 88:1772ysb (1978) Shchukin et al, 87:29032u (1977) Kondo, 81:68585x (1974) Malkawa, 7–8:68563p (1974) Yazawa.

Chem. Abstracts General Subject Index, vol. 92, 1980–8th Coll (to 1967), Bifdobacterium-: B. Bifidum, B. Infantis, B. Adolescentis, B. Pseudolongum, B. Longum, B. Breve, B. Ruminale, B. Thermophilum, B. Globosum, B. Angulatum, B. Catenulatum, B. Dentium, B. Pullorum, B. Asteroides, B. Fragilis et al.

Chem. Abstracts General Subject Index vol. 92, 1980–8th Coll (to 1967), Capsules–microcapsules.

*Primary Examiner*—Shep K. Rose
*Attorney, Agent, or Firm*—Vogt & O'Donnell

[57] ABSTRACT

A microcapsule containing a microorganism. It contains a microorganism of the genus Lactobacillus and/or Bifidobacterium and/or other geni of the intestinal flora coated with a fat which is solid at body temperature.

8 Claims, No Drawings

MICROCAPSULE CONTAINING A MICROORGANISM AND A PROCESS FOR ITS PRODUCTION

This invention relates to a microcapsule containing microorganisms and to a process for its production.

The systematic use of antibiotics involves certain dangers insofar as it alters the intestinal flora and promotes the development of mutants resistant to antibiotics. The intestinal flora is made up of more than 80% of lactobacilli and bifidobacteria. The latter, which were originally called *Lactobacillus bifidus*, now form the separate genus Bifidobacterium. Bifidobacteria are characteristic of the intestinal flora of healthy babies. Attempts are at present being made to replace antibiotics by pure cultures of microorganisms capable of regenerating or reconstituting a healthy and vigorous flora which prevents pathogenic germs from developing. However, a microorganism of the genus Lactobacillus is generally anaerobic whilst a microorganism of the genus Bifidobacterium is strictly anaerobic with the result that it is difficult to keep them alive outside their natural medium, which is the intestine, and moreover to preserve them for prolonged periods in medicaments.

The present invention satisfies the need for a means of presenting, conserving and orally applying microorganisms of the intestinal flora. The invention provide this means in the form of a microcapsule containing microorganisms.

The microcapsule according to the invention is characterised in that it contains microorganisms of the genus Lactobacillus and/or Bifidobacterium and/or other geni of the intestinal flora coated with a fat solid at body temperature.

It has been found that it is possible to present these microorganisms in the form of microcapsules of solid fat in which they retain all their vitality, even after these microorganisms have been kept for prolonged periods at ambient temperature, in a refrigerator at 5° C. or in a freezer at −30° C. for example.

It has been found that it is possible to administer these microcapsules orally and that most of their microorganism content arrives intact in the intestinal tract without having been damaged by the strongly acid conditions (pH below 2) prevailing in the stomach. Thus, a reputedly delicate microorganism, such as Bifidobacterium for example, may now be preserved and administered without difficulty. Accordingly, the present invention represents a decisive step forward along the path leading to the replacement of antibiotics by natural means for reconstituting a sound and vigorous intestinal flora which itself prevents the proliferation of pathogenic microorganisms.

The present invention also relates to a process for producing these microcapsules which is characterised in that a dispersion of microorganisms of the genus Lactobacillus and/or Bifidobacterium and/or other geni of the intestinal flora in molten fat having a melting point above body temperature is prepared, the dispersion is sprayed into a chamber where a temperature below the melting point of the fat prevails and the solidified microcapsules are collected.

It is essential that the micriorganisms do not come into contact with air. A fat which is solid at ambient temperature keeps them away from air during any handling which they undergo before ingestion. This fat should also remain solid during the passage through the stomach so that the germs which it contains remain protected against the acidity prevailing in the stomach. Thus, it is preferred to use a vegetable edible fat, particularly a hydrogenated fat of palm, peanut, coconut, cocoa, rape or soya, or animal fat having a melting point of from 40° to 60° C. It is not recommended to use a fat which has a melting point above 60° C. because the necessary temperature for liquefying this fat and preparing the emulsion would be in danger of destroying the microorganisms whose viability it is precisely desired to maintain.

The microcapsules preferably contain from $10^7$ to $10^{10}$ revivifiable individuals or germs of Lactobacillus and/or Bifidobacterium per gram of fat. They may contain in particular the microorganisms *Bifidobacterium (B.) animalis* P23 or *B. sui* Su 806, or *B. infantis* Bi 1 and Bi 5 and/or *B. longum* Bl 10 and Bl 11 and/or *B. breve* Bbr 8 obtained from the Institute of Agricultural Microbiology of the University of Bologna, Italy. They preferably have a diameter of from 0.1 to 0.5 mm. A smaller diameter does not have any significant disadvantages except that the surface-to-volume ratio is greater which means a greater loss of microorganisms incompletely fixed in the mass. A larger diameter does not have any significant disadvantages either, apart from the fact that it is in danger of preventing passage through small holes, such as the holes in the teats of feeding bottles for example. In order to improve the flow properties of a powder formed from a quantity of these microcapsules or to prevent as far as possible the formation of agglomerates of microcapsules, the microcapsules may be coated with a layer of an anti-agglomerating agent, such as a protein for example. Very good results are obtained in particular with an outer layer of zein or of a protective agent of the type used in galenics.

To carry out the process for producing the microcapsules according to the invention, it is possible to culture the microorganisms in a suitable liquid medium until a sufficient quantity of cells has been produced and to collect the cells thus produced by centrifuging. The cells may then be finely dispersed either as such or after freeze-drying in molten fat having a melting point of from 40° to 60° C. in a quantity of from $10^7$ to $10^{10}$ individuals or germs per gram of fat. To form the microcapsules, the dispersion may be sprayed together with liquid nitrogen at the top of a chamber filled with sterilised air for example. However, in one preferred embodiment, which also lends itself to the production of any microcapsules of fat containing a delicate active agent sensitive to air, heat and acids for example, the dispersion of active agent in the molten fat is sprayed into the top of a chamber which has an upper moderate-temperature zone and a lower low-temperature zone.

It has been found that it is possible in this way to obtain highly spherical microcapsules differing very little from one another in size.

The dispersion is preferably sprayed into the top of the chamber under a pressure of from 3 to 6 bars. Under a pressure of less than 3 bars, the capsules differ excessively in size whereas, under a pressure of more than 6 bars, the capsules obtained are too small. The temperature prevailing in the upper zone of the chamber may be between about −10° C. and the melting point of the fat used, although a temperature of from 15° to 25° C. is preferably used. If the temperature prevailing in the upper part of the chamber is too low, the capsules obtained differ excessively in size. Accordingly, it is important to observe the conditions under which the capsules are formed in the best possible way before being hardened by the low temperature prevailing in the lower zone. The height of the upper zone or "formation zone" of the balls which may be maintained above the lower zone or "solidification zone" of the capsules will depend on the total height available, although it will preferably be of the order of at least one meter. The low temperature which has to prevail in the lower zone of the chamber may be generated by spraying liquid nitrogen therein. The nitrogen may be sprayed from the bottom of the chamber for example. The pressure and the input of nitrogen will be selected in dependence upon the height of the nitrogen mist which it is desired to obtain.

Irrespective of the method by which the dispersion is sprayed, the fine droplets formed and then solidified on contact with air, nitrogen or other cold medium provided in the chamber may be collected at the bottom of the chamber on a conveyor or in a tank of which the temperature does not exceed 5° to 15° C. They may be packed, conserved and used as such or may first be coated with a layer of material which prevents them from sticking to one another, i.e. an anti-agglomerating agent. This agent may be a protein for example, particularly zein, or a protective agent of the type used in galenics. This layer may be applied by spraying a solution of this agent onto the microcapsules in a fluidised bed for example. The microcapsules may be kept in a refrigerator, in a deep freeze or at ambient temperature.

The microcapsules according to the present invention may be directly administered orally or may be mixed with certain solid or liquid foods. For example, they may be mixed with the milk used to fill the feeding bottle of a baby, their dimensions enabling them to pass through the hole(s) of the teat.

The invention is illustrated by the following Examples in which the percentages quoted represent percent by weight unless otherwise indicated.

EXAMPLE 1

In a 100 liter tank, 80 liters of TSAR culture medium having the following composition (in percent) are prepared:

Yeast extract: 0.25%
Trypticase: 1.00
Phytone: 0.50%
Glucose: 1.50
L-cysteine HCl: 0.05
$K_2HPO_4$: 0.25
$ZnSO_4$: 0.025
$FeCl_3$: trace
Water: balance to 100%

This culture medium is inoculated with 1 liter of a 20 h culture of *Bifidobacterium animalis* P 23 obtained from the Institute of Agricultural Microbiology of the University of Bologna, Italy. The whole is then incubated for 12 h at 37° C. The culture broth is centrifuged and 240 g of cells are collected. They are diluted in 250 ml. of skimmed milk to which 7% of lactose has been added. The mixture is frozen with liquid nitrogen and freeze-dried overnight at 40° C. A 5% dispersion of the powder obtained is prepared in hydrogenated vegetable fat having a melting point of 42° C. and liquefied at 45° C.

The dispersion is injected at 45° C. under a pressure of 4 bars at the same time as liquid nitrogen in a quantity of 1 part of dispersion to 5 parts of nitrogen into the top of a vertical cylinder 1.5 m in diameter and 10 m tall. At the bottom of the the cylinder there is a container filled with liquid nitrogen in which microcapsules ranging from 0.1 to 0.5 mm in diameter are collected.

One third of the microcapsules are placed in a fluidised bed and the bed is sprayed with an 8% alcoholic solution of zein in such a quantity that the layer of zein formed around the microcapsules represents 5% of their weight.

Similarly, using a mixture of Eudragit L and S (anionic polymers of methacrylic acid and esters of methacrylic acid) in the form of a 10% solution in isopropyl alcohol, a second third of the microcapsules is coated with a layer of mixture representing from 5 to 10% of their weight.

After 6 months in a refrigerator at 5° C. and at ambient temperature, the three types of microcapsules still contain more than $10^8$ living microorganisms per gram.

EXAMPLE 2

The procedure is as described in Example 1, except that the microcapsules are collected on a conveyor belt cooled to 5° C. at the bottom of the cylinder.

EXAMPLE 3

The procedure is as described in Example 1, except that the TSAR culture medium is replaced by a culture medium having the following composition (in percent):

Yeast extracts: 0.10%
Trypticase: 0.25
Bacto soytone: 0.25
Glucose: 0.50
L-cysteine HCl: 0.001
$K_2HPO_4$: 0.10
$MgCl_2$: 0.002
$ZnSO_4$: 0.001
$FeCl_3$: 0.0002
Permeate of whey: 4.00
Corn steeping liquor: 0.50
Distilled water: balance to 100%

EXAMPLE 4

The procedure is as described in Example 1, except that the culture medium is inoculated with 1 liter of a culture of *Lactobacillus acidophilus* instead of *Bifidobacterium animalis*.

EXAMPLE 5

The procedure is as described in Example 1, except that the dispersion is injected into the top of a vertical cylinder 1.5 m in diameter and 2.5 m rather than 10 m tall.

EXAMPLE 6

Rats are administered dry the zein-coated microcapsules stored for 6 months of Example 1 in a quantity of 1 g per meal and 1 meal per day. On the following day, billions of bifidobacteria are counted in the stools of rats given the microcapsules (treated rats) whereas the stools of rats which have not ingested any microcapsules (untreated rats) do not contain any bifidobacteria. The following Table gives the result of comparative analyses of the stools of treated and untreated rats:

|  | Before treatment | | After 7 days' treatment | |
|---|---|---|---|---|
|  | Total number of germs (mil/g) | Bifidus content (%) | Total number of germs (mil/g) | Bifidus content (%) |
| Untreated rats | 5000 | 0 | 6500 | 0 |
| Treated rats | 5500 | 0 | 7500 | 75 |

A cross-breeding test of the DNA of laboratory cultures with the DNA of the bifidobacteria isolated from the stools confirms that the two microorganisms are the same. Accordingly, the bifidobacteria survived storage and passage through the stomach and multiplied in the digestive tract of the rat.

EXAMPLE 7

For administration to piglets, microcapsules containing the microorganism *Bifidobacterium sui* Su 806 obtained from the Institute of Agricultural Microbiology of the University of Bologna are prepared in accordance with the invention.

EXAMPLE 8

For administration to infants in clinical tests, microcapsules containing the microorganisms *Bifidobacterium infantis* Bi 1 and Bi 5, *Bifidobacterium longum* Bl 10 and Bl 11 and *Bifidobacterium breve* Bbr 8 obtained from the Institute of Agricultural Microbiology of the University of Bologna are prepared in accordance with the invention.

To this end, a freeze-dried biomass of the above-mentioned microorganisms is prepared. 0.25 part of the freeze-dried biomass is dispersed in 5 parts of molten hydrogenated palm oil at 45° C. Using a SPRAYING SYSTEM CO 5510/422 nozzle, 75 l/h of dispersion are sprayed under a pressure of 5.5 bars into the top of a 2.7 m tall tank funnel-shaped at its lower end. A temperature of 26° C. is maintained in the upper part of the tank. A temperature of −145° C. is maintained in the lower part of the tank by injecting therein from the bottom and under a pressure of 1.6 bars, using a deflector nozzle, a mist of liquid nitrogen of which the peak finishes 1.2 m below the nozzle used to inject the fat. Round microcapsules which range from 0.1 to 0.2 mm in diameter and which contain $4.10^8$ revivifiable germs per g are collected at the bottom of the funnel.

EXAMPLES 9-12

Microcapsules are prepared in the same way as described in Example 8, except that the dispersion and the nitrogen are injected under different pressure ($P_D$ and $P_{N2}$) and the temperature in the upper part ($T_H$) and lower part ($T_B$) of the tank are also varied. The conditions under which the various tests were conducted and the results, as observed under a microscope, are set out in the following Table:

| Example No. | $P_D$ (bars) | $P_{N2}$ (bars) | $T_H$ (°C.) | $T_B$ (°C.) | Results (under a microscope) |
|---|---|---|---|---|---|
| 9 | 3.5 | 1.3 | −9.5 | −110 | Capsules from 0.2 to 0.5 mm in diameter. Little difference in size. Good sphericity |
| 10 | 10 | 1.3 | −22.3 | −94.2 | Capsules <0.1 mm in diameter. Too many minuscule balls. Rodlets in abundance. |
| 11 | 4 | 1.6 | 21 | −150 | Spherical capsules 0.3 to 0.5 mm in diameter. Little difference in size. |
| 12 | 10 | 1.6 | 19.6 | −143 | Spherical capsules <0.1 mm in diameter. |

Addendum: The strains *B. animalis* P 23 and *B. sui* Su 806 were deposited in the American Type Culture Collection and appear in the catalogue of 1978 under ATCC No 27 536 and 27 686. The strains *B. infantis* Bi 5, *B. breve* Bbr 8, *B. longum* Bl 10 and Bl 11 were deposited on 29th Oct, 1979 in the "Collection Nationale de Microorganismes" of the "Institut Pasteur" in France and given the respective numbers I-100, I-101, I-102 and I-103.

We claim:

1. A process for the production of microcapsules of fat containing microorganisms of the genus Lactobacillus and/or Bifidobacterium and/or other geni of the intestinal flora comprising forming a dispersion of the microorganisms in molten fat having a melting point of from 40° to 60° C. with from $10^7$ to $10^{10}$ individuals or germs of Lactobacillus and/or Bifidobacterium per gram of fat; spraying the dispersion into the upper portion of a chamber under a pressure of from 3 to 6 bars, said chamber having an upper moderate-temperature zone of at least one meter in height maintained at a temperature between −10° C. and the melting temperature of the fat and a lower low-temperature zone; and collecting the solidified microcapsules.

2. A microcapsule containing a microorganism prepared by the process of claim 1 wherein the microcapsule contains the microorganisms *Bifidobacterium* (*B.*) *animalis* P 23 or *B. sui* Su 806 or *B. infantis* Bi 1 and Bi 5 and/or *B. longum* Bl 10 and Bl 11 and/or *B. breve* Bbr 8 obtained from the Institute of Agricultural Microbiology of the University of Bologna, Italy, is coated with a fat having a melting point of from 40° to 60° C., has a diameter of from 0.1 to 0.5 mm and wherein the concentration of the microorganisms in the microcapsule is from $10^7$ to $10^{10}$ revivifiable individuals or germs per gram of fat.

3. A process as claimed in claim 1, wherein freeze-dried microorganisms are dispersed in the molten fat.

4. A process as claimed in claim 1, wherein a dispersion of the microorganism *Bifidobacterium animalis* P 23 or *B. sui* Su 806 or *B. infantis* Bi 1 and Bi 5 and/or *B. longum* Bl 10 and Bl 11 and/or *B. breve* Bbr 8 obtained from the Institute of Agricultural Microbiology of the University of Bologna, Italy, is prepared.

5. A process as claimed in claim 1, wherein the microcapsules are coated with an anti-agglomerating agent, particularly zein.

6. A process as claimed in claim 1, wherein the low temperature prevailing in the lower zone is generated by spraying liquid nitrogen therein.

7. A microcapsule as claimed in claim 2, wherein the fat is an animal or vegetable fat, particularly a hydrogenated fat of palm, peanut, coconut, cocoa, rape or soya.

8. A microcapsule as claimed in claim 2, wherein it has an outer layer of an anti-agglomerating agent, particularly zein.

* * * * *